(12) United States Patent
Hokii et al.

(10) Patent No.: US 9,102,813 B2
(45) Date of Patent: Aug. 11, 2015

(54) FLUOROALUMINOSILICATE GLASS POWDER AND PRODUCTION METHOD THEREOF

(71) Applicant: GC CORPORATION, Bunkyo-ku (JP)

(72) Inventors: Yusuke Hokii, Saitama (JP); Katsuhito Kato, Shinjuku (JP); Futoshi Fusejima, Kitamoto (JP)

(73) Assignee: GC CORPORATION, Bunkyo-ku (JP)

( * ) Notice: Subject to any disclaimer, the term of this patent is extended or adjusted under 35 U.S.C. 154(b) by 0 days.

(21) Appl. No.: 14/039,461

(22) Filed: Sep. 27, 2013

(65) Prior Publication Data
US 2014/0090580 A1 Apr. 3, 2014

(30) Foreign Application Priority Data
Sep. 28, 2012 (JP) ................................. 2012-217619

(51) Int. Cl.
| | | |
|---|---|---|
| C04B 20/10 | (2006.01) | |
| C08K 3/40 | (2006.01) | |
| A61K 6/00 | (2006.01) | |
| A61K 6/083 | (2006.01) | |
| C03C 3/112 | (2006.01) | |
| C03C 4/00 | (2006.01) | |
| C03C 12/00 | (2006.01) | |
| C04B 28/28 | (2006.01) | |
| C03C 23/00 | (2006.01) | |
| A61K 6/02 | (2006.01) | |
| C04B 111/00 | (2006.01) | |

(52) U.S. Cl.
CPC .................. *C08K 3/40* (2013.01); *A61K 6/0091* (2013.01); *A61K 6/025* (2013.01); *A61K 6/0835* (2013.01); *C03C 3/112* (2013.01); *C03C 4/0021* (2013.01); *C03C 12/00* (2013.01); *C03C 23/0095* (2013.01); *C04B 20/107* (2013.01); *C04B 28/28* (2013.01); *C04B 2111/00836* (2013.01)

(58) Field of Classification Search
CPC ........ C03C 3/112; C03C 3/062; C03C 3/118; C03C 3/091; C03C 3/083; C03C 3/093; C03C 8/02; C03C 8/04; C03C 8/14; C03C 8/24; C03C 8/245; C03C 8/06
USPC ........................ 501/14, 15, 21, 25, 57, 59, 68
See application file for complete search history.

(56) References Cited

U.S. PATENT DOCUMENTS

| | | | | |
|---|---|---|---|---|
| 4,376,835 A | * | 3/1983 | Schmitt et al. ................. | 523/116 |
| 4,775,592 A | * | 10/1988 | Akahane et al. .............. | 428/406 |
| 6,437,019 B1 | * | 8/2002 | Rusin et al. ................... | 523/117 |
| 2006/0160919 A1 | * | 7/2006 | Brugger et al. ................ | 523/116 |

FOREIGN PATENT DOCUMENTS

| | | |
|---|---|---|
| EP | 1 634 561 A1 | 3/2006 |
| JP | 5-331017 A | 12/1993 |
| JP | 6-321724 A | 11/1994 |

OTHER PUBLICATIONS

Extended European Search Report issued on Feb. 4, 2014 in the corresponding European Patent Application No. 13004696.4.
C. M. Crowley, et al., "Influence of acid washing on the surface morphology of ionomer glasses and handling properties of glass ionomer cements", Journal of Materials Science: Materials in Medicine, Kluwer Academic Publishers, Bo. vol. 18, No. 8, XP019529202, Mar. 27, 2007, pp. 1497-1506.

* cited by examiner

*Primary Examiner* — Noah Wiese
(74) *Attorney, Agent, or Firm* — Oblon, McClelland, Maier & Neustadt, L.L.P.

(57) ABSTRACT

[Problems to be Solved]
To provide fluoroaluminosilicate glass powder enabling to improve acid resistance of dental glass ionomor cement and a production method thereof.
[Solution]
A lanthanum compound eluted in the presence of polycarboxylic acid and water exists only in a surface layer of a fluoroaluminosilicate glass powder. An amount of the fluoroaluminosilicate glass powder is preferably 1 to 5% by weight in terms of oxide. The fluoroaluminosilicate glass powder is produced by mixing an aqueous solution of a lanthanum compound and a fluoroaluminosilicate glass powder not containing lanthanum, and heating them. The aqueous solution of lanthanum compound is an aqueous solution of a water solvable lanthanum compound, preferably an aqueous solution of lanthanum nitrite and/or an aqueous solution of lanthanum chloride.

12 Claims, No Drawings

FLUOROALUMINOSILICATE GLASS POWDER AND PRODUCTION METHOD THEREOF

BACKGROUND OF THE INVENTION

1. Field of the Invention

The present invention relates to a fluoroaluminosilicate glass powder enabling to improve an acid resistance of a dental glass ionomer cement, and a production method thereof.

2. Description of the Conventional Art

The dental glass ionomer cement has excellent affinity for a living body, adhesion to tooth structure, and excellent esthetics since a set body is translucency. In addition, the dental glass ionomer cement has a merit that the cement slowly releases fluoride to strengthen a tooth structure, so that it has been widely used in various applications of dental field. The dental glass ionomer cement is a dental cement including a fluoroaluminosilicate glass powder and polycarboxylic acid aqueous solution as main components. More particularly, the polycarboxylic acid aqueous solution dissolves a surface one layer of the fluoroaluminosilicate glass powder and liberates metals in the glass (alkali metal, alkali-earth metal, and aluminum) as ions. These ions combine with a carboxyl group in the polycarboxylic acid by ionic bonding and form a crosslinking structure to be set by gelation (hereinafter, it may be called as an ionomer reaction).

However, it is known that, after setting, the dental glass ionomer cement is dissolved a little by an acid. It is thought that this reaction is not a problem in general, but by cases, it is concerned that the reaction becomes a problem in some portions, such as a space between teeth and a space of a dental restorative material, where the concentration of an acid has become extremely high by caries. Therefore, it is desired to develop a dental glass ionomer cement having higher acid resistance.

The present inventors confirmed that when a fluoroaluminosilicate glass powder containing lanthanum is used, the glass and a matrix after setting are chemically stabilized and acid resistance improves (refer to Japanese Patent Application Laid-Open No. H5-331017 and Japanese Patent Application Laid-Open No. H6-321724). However, there is a problem that when lanthanum having a large ionic radius is contained in a glass, the refractive index of the glass powder becomes high and the difference of the refractive index to the polycarboxylic acid aqueous solution, which is cement liquid, becomes large, so that the transparency of the set body lowers.

SUMMARY OF THE INVENTION

Problem to be Solved by the Invention

The present invention is directed to provide a fluoroaluminosilicate glass powder enabling to obtain dental glass ionomer cement not lowering the transparency while improving the acid resistance of the set body, and the production method thereof.

The present inventors have been carrying out earnest works to solve the above problems and as a result, they found out followings to complete the present invention. That is, they focused the point that, in a dental glass ionomer cement, a surface one layer of the fluoroaluminosilicate glass powder is dissolved by polycarboxylic acid, and metal ions in the dissolved glass powder crosslink the polycarboxylic acid and set the cement. Thus, if a lanthanum compound exists only in a surface layer of the glass powder, extra lanthanum does not exist in the glass power after setting, so that the glass powder can stay in a state having a low refractive index. As a result, keeping the good transparency of the set body, the acid resistance of the cement can improve.

That is, the present invention relates to a fluoroaluminosilicate glass powder in which a lanthanum compound exists only in a surface layer of the glass. The lanthanum compound is eluted in the presence of polycalboxylic acid and water. The amount of the lanthanum compound in the fluoroaluminosilicate glass powder is preferably 1 to 5% by weight in terms of oxide. The present invention also relates to a production method of the fluoroaluminosilicate glass powder containing a lanthanum compound. The production method includes, mixing an aqueous solution containing a lanthanum compound and a fluoroaluminosilicate glass powder not containing lanthanum compounds, and heating them. As the lanthanum compound, a water-soluble lanthanum compound, preferably an aqueous solution of lanthanum nitrate and/or lanthanum chloride is used.

Effect of the Invention

The fluoroaluminosilicate glass powder according to the present invention is an excellent fluoroaluminosilicate glass powder enabling to obtain a set body of dental glass ionomer cement not lowering the transparency while improving the acid resistance of the set boy. The production method of the fluoroaluminosilicate glass powder according to the present invention is a simple method in which an aqueous solution containing a lanthanum compound is mixed with the fluoroaluminosilicate glass powder not containing lanthanum, and heated.

DETAILED DESCRIPTION OF THE INVENTION

In the fluoroaluminosilicate glass powder according to the present invention, a lanthanum compound exists only in the surface layer of the fluoroaluminosilicate glass powder not containing lanthanum, where the lanthanum compound is eluted in the presence of a polycarboxylic acid and water. As a basic glass power for that, a conventional fluoroaluminosilicate glass powder not containing lanthanum can be used without particular limitations. Among these, the following component is preferable. That is, as its main component, $Al^{3+}$ of 10 to 25% by weight, $Si^{4+}$ of 5 to 30% by weight, $F^-$ of 1 to 30% by weight, $Sr^{2+}$ of 0 to 20% by weight, $Ca^{2+}$ of 0 to 20% by weight, and alkali earth metal ($Na^+$, $K^+$, and the like) of 0 to 10% by weight, with respect to the total weight of the glass. The preferable fluoroaluminosilicate glass powder is produced by mixing and melting a raw material containing the above components, cooling and pulverizing, and adjusting the powder to have about 0.02~20 μm average particle size.

The lanthanum compound eluted in the presence of polycarboxylic acid and water can be present only in the surface layer by mixing an aqueous solution containing a lanthanum compound and a fluoroaluminosilicate glass powder, and heating them. In this case, since water is used as a solvent, the lanthanum compound needs to be water-solvable, so that lanthanum nitrite and/or lanthanum chloride is preferable.

At this time, an aqueous solution, in which the treatment concentration of the lanthanum compound in the aqueous solution with respect to the fluoroaluminosilicate glass powder not containing lanthanum is prepared so as to be about 2 to 10% by weight. Then, the aqueous solution and the fluoroaluminosilicate glass powder not containing lanthanum are mixed and heated at 100 to 300° C. When the treatment concentration is less than 2% by weight, there is a tendency that the amount of the lanthanum compound existing only in the surface layer and eluted in the presence of a polycarboxylic acid and water, is insufficient. When the treatment concentration is more than 10% by weight, there is a tendency that lanthanum fluoride is formed and the transparency deteriorates.

After heating, the obtained powder is dried, if necessary and then, the fluoroaluminosilicate glass powder containing the lanthanum compound only in the surface layer is obtained, where the lanthanum compound is eluted in the presence of polycarboxylic acid and water. The amount of lanthanum compound eluted in the presence of the polycarboxylic acid and water is preferably 1 to 5% by weight in terms of oxide with respect to the total weight of the fluoroaluminosilicate glass powder. When the amount of the lanthanum compound is less than 1% by weight, an improvement effect of the acid resistance is hardly obtained. When the amount of the lanthanum compound is more than 5% by weight, there is a tendency that the lanthanum fluoride is easily formed at the same time and the transparency deteriorates.

The fluoroaluminosilicate glass powder not containing lanthanum, which is used in the production method of the fluoroaluminosilicate glass powder according to the present invention, can be surface-treated with an acid or a fluoride using a similar method in the conventional fluoroaluminosilicate glass powder. By surface-treating with the acid and the fluoride, fluidity of the cement mud increases, operability is improved, and further the setting is more sharpened. As the acid for the treatment, for example, phosphoric acid, hydrochloric acid, pyrophosphate acid, tartaric acid, citric acid, glutaric acid, malic acid, acetic acid, and the like, can be used. Further, in addition, primary phosphate and secondary phosphate, which are an acidic substance, can be included. Further, as the fluoride used in the treatment, aluminum fluoride, zinc fluoride, tin fluoride, zirconium fluoride, sodium bifluoride, acid potassium fluoride, and the like, can be used.

Of course, the fluoroaluminosilicate glass powder according to the present invention can be also used in the conventional glass ionomer cement composition and a resin-reinforced glass ionomer cement. The conventional glass ionomer cement is polymerized by mixing a powder and a liquid. A polymerizable monomer and a chemical polymerization catalyst or a light polymerization catalyst are blended in the resin-reinforced glass ionomer cement. In these cases, there also is an effect to improve the acid resistance of the set body of the cement.

In addition, of course, the conventional used pigments, and the like, can be suitably blended in the fluoroaluminosilicate glass powder according to the present invention if necessary.

EXAMPLES

Preparation of Fluoroaluminosilicate Glass Powder not Containing Lanthanum

The bending amounts of the fluoroaluminosilicate glass powder I, II and III are shown in Table 1.

TABLE 1

| | | Fluoroaluminosilicate glass powder | | |
| --- | --- | --- | --- | --- |
| | | I | II | III |
| Aluminum Oxide | (g) | 21 | 23 | 22 |
| Silicic anhydride | (g) | 39 | 41 | 43 |
| Calcium fluoride | (g) | 12 | 10 | 12 |
| Calcium phosphate | (g) | 14 | 13 | 15 |
| Strontium carbonate | (g) | 9 | 13 | 8 |
| Sodium fluoride | (g) | 5 | 0 | 0 |

About the fluoroaluminosilicate glass powders I and III, the raw materials are thoroughly mixed, and the glass is melted in a high temperature electric furnace at 1200° C. for keeping time of 5 hours. After melting, the glass is cooled, pulverized for 10 hours using a ball mill, and then sieved by No. 200 mesh (ASTM) and thereby, the powder is made. The after sieved powder is made to be the fluoroaluminosilicate glass powder not containing lanthanum. About fluoroaluminosilicate glass powder II, the same operation is carried out as the fluoroaluminosilicate glass powder I and III, excepting the melting temperature of 1100° C.

As the comparative examples 1 to 3, the conventional fluoroaluminosilicate glass powder not containing lanthanum is used. As the comparative examples 4 to 7, the glass powder, in which the lanthanum compound eluted in the presence of polycarboxilic acid and water does not exist in the surface layer, is used.

The lanthanum compound dissolved in aqueous solution (examples 1 to 13) and yttrium nitrate (comparative examples 4 to 7) are added to the fluoroaluminosilicate glass powder not containing lanthanum, according to the treatment concentration in Table 2 and Table 3. Here, yttrium is a rare-earth metal and yttrium nitrate takes a trivalent state when yttrium becomes to an ion state. Then, the glass powders added with the lanthanum compound and yttrium are thoroughly mixed in a mortar and dried at the heating temperature in Table 2 and Table 3.

<Setting Method of Dental Glass Inomor Cement>

To 0.34 g of the fluoroaluminosilicate glass powder in the example and the comparative examples, 0.1 g of a conventional glass ionomer cement liquid (trade name: Fuji IXGP EXTRA produced by GC corporation) is added, and the setting bodies of the glass ionomor cement composition are obtained.

<Evaluation of Acid Resistance>

The water resistance and acid resistance of the set cement body are evaluated based on the acid solubility test in JIS T6609-1. The dental cement composition after kneading is filled in a mold made of polymethylmethacrylate having a hole with 5 mm diameter and 2 mm depth, pressure-contacted through a film, and allowed to stand in a thermostatic bath at temperature 37° C. and under a relative humidity of 100% for 24 hours. Then, the surface of the set cement body is polished to be flat, remaining integral with the mold, by a waterproof abrasive paper of #1200 under feeding water. The initial thickness between the surface of the set cement body and the surface on the opposite side is measured. The testing pieces are dipped in lactic acid/sodium lactate buffer solution of 0.1 mol/L (pH 2.74) for 24 hours and then, the thickness is measured in the same way. The reduced amount is evaluated.

<Evaluation of Transparency>

The kneaded cement is filled in a metal mold and a set body with a diameter of 15 mm and a thickness of 0.5 mm is obtained. After 10 min. from the start of kneading, a white background and a black background are measured respectively by a colorimeter (Spectrophotometer CM-3610d produced by KONICA MINOLTA, INC.). The value of L*

(black) and L* (white) in CIE-L*a*b* color system are calculated and ΔL=L* (white)−L* (black) is made to be a transparency indicator.

the lanthanum compound to be eluted in a presence of polycarboxylic acid and water exists only in a surface layer of the powder.

TABLE 2

|  |  | Example 1 | Example 2 | Example 3 | Example 4 | Example 5 | Example 6 | Example 7 |
|---|---|---|---|---|---|---|---|---|
| Fluoroaluminosilicate glass |  |  |  |  | Glass I |  |  |  |
| Lanthanum compound Treatment concentration to glass powder (% by weight) | Lanthanum nitrite | 2.5 | 5 | 7.5 | 10 | 10 |  |  |
|  | Lanthanum chloride |  |  |  |  |  | 5 | 10 |
| Heating temperature (° C.) |  | 200 | 200 | 200 | 200 | 200 | 200 | 200 |
| Lanthaum compound concentration in glass (in terms of oxide, % by weight) |  | 1 | 2 | 2.6 | 4.1 | 4 | 1.6 | 3.3 |
| Acid solubility test (JIS 16609-1: 2005) amount of dissolution (mm) |  | 0.124 | 0.112 | 0.106 | 0.086 | — | 0.108 | 0.089 |
| Transparency of set body (0.5 mm thickness) ΔL |  | 30 | 30 | 30 | 30 | 15 | 30 | 30 |

|  |  | Example 8 | Example 9 | Example 10 | Example 11 | Example 12 | Example 13 |
|---|---|---|---|---|---|---|---|
| Fluoroaluminosilicate glass |  |  | Glass II |  |  | Glass III |  |
| Lanthanum compound Treatment concentration to glass powder (% by weight) | Lanthanum nitrite | 2.5 | 5 | 10 | 2.5 | 5 | 10 |
|  | Lanthanum chloride |  |  |  |  |  |  |
| Heating temperature (° C.) |  | 200 | 200 | 200 | 200 | 200 | 200 |
| Lanthaum compound concentration in glass (in terms of oxide, % by weight) |  | 1 | 2 | 3.9 | 1.1 | 1.5 | 4 |
| Acid solubility test (JIS 16609-1: 2005) amount of dissolution (mm) |  | 0.045 | 0.032 | 0.03 | 0.055 | 0.04 | 0.031 |
| Transparency of set body (0.5 mm thickness) ΔL |  | 25 | 25 | 25 | 28 | 28 | 28 |

TABLE 3

|  |  | Comparative example 1 | Comparative example 2 | Comparative example 3 | Comparative example 4 | Comparative example 5 | Comparative example 6 | Comparative example 7 |
|---|---|---|---|---|---|---|---|---|
| Fluoroaluminosilicate glass |  | Glass I | Glass II | Glass III | Glass II | Glass II | Glass III | Glass III |
| Lanthanum compound Treatment concentration to glass powder (% by weight) | Yttrium nitrate |  |  |  | 2.5 | 7.5 | 2.5 | 7.5 |
| Heating temperature (° C.) |  |  |  |  | 200 | 200 | 200 | 200 |
| Yttrium oxide concentration in glass (in terms to oxide, % by weight) |  |  |  |  | 0.7 | 1.8 | 0.8 | 2 |
| Acid solubility test (JIS T6609-1: 2005) amount of dissolution (mm) |  | 0.133 | 0.055 | 0.065 | 0.054 | 0.056 | 0.066 | 0.064 |
| Transparency of set body (0.5 mm thickness) ΔL |  | 30 | 25 | 28 | 25 | 25 | 28 | 28 |

As clearly shown in the examples and the comparative examples, it can be understood as follows. That is, the acid resistance of the set body of the dental glass ionomer cement using the fluoroaluminosilicate glass powder produced by the production method of the present invention is improved while maintaining the transparency, as comparing with the conventional fluoroaluminosilicate glass powder not containing the lanthanum compound eluted in the presence of polycarboxylic acid and water.

What is claimed is:

1. Fluoroaluminosilicate glass powder, comprising a lanthanum compound directly bonded to the powder, wherein the lanthanum compound to be eluted in a presence of polycarboxylic acid and water exists only in a surface layer of the powder.

2. The fluoroaluminosilicate glass powder according to claim 1, wherein of the lanthanum compound is present in an amount of 1 to 5% by weight in terms of oxide.

3. A method of producing fluoroaluminosilicate glass powder, comprising a lanthanum compound directly bonded to the powder, wherein a lanthanum compound to be eluted in a presence of polycarboxilic acid and water exists only in a surface layer of the powder, the method comprising;

mixing an aqueous solution comprising a lanthanum compound and a fluoroaluminosilicate glass powder not containing lanthanum, and heating the mixture.

4. The production method of fluoroaluminosilicate glass powder according to claim 3, wherein the lanthanum compound is a water soluble lanthanum compound.

5. The production method of fluoroaluminosilicate glass powder according to claim 4, wherein the water soluble lanthanum compound is in an aqueous solution and the water soluble lanthanum compound is lanthanum nitrate and/or lanthanum chloride.

6. The method according to claim 3, wherein the heating is performed at a temperature of 100 to 300° C.

7. The fluoroaluminosilicate glass powder according to claim 1, wherein the fluoroaluminosilicate glass powder comprises $Al^{3+}$ of 10 to 25% by weight, $Si^{4+}$ of 5 to 30% by weight, $F^-$ of 1 to 30% by weight, $Sr^{2+}$ of 0 to 20% by weight, $Ca^{2+}$ of 0 to 20% by weight, and alkali earth metal of 0 to 10% by weight, with respect to the total weight of the glass powder.

8. The method according to claim 3, wherein the fluoroaluminosilicate glass powder comprises $Al^{3+}$ of 10 to 25% by weight, $Si^{4+}$ of 5 to 30% by weight, $F^-$ of 1 to 30% by weight, $Sr^{2+}$ of 0 to 20% by weight, $Ca^{2+}$ of 0 to 20% by weight, and alkali earth metal of 0 to 10% by weight, with respect to the total weight of the glass powder.

9. The fluoroaluminosilicate glass powder according to claim 1, wherein the fluoroaluminosilicate glass powder has an average particle size of 0.02 to 20 µm.

10. The method according to claim 3, wherein the fluoroaluminosilicate glass powder has an average particle size of 0.02 to 20 µm.

11. The method according to claim 3, wherein the lanthanum compound is present in the aqueous solution in an amount of 2 to 10% by weight of the aqueous solution.

12. The method according to claim 3, further comprising, after the heating, drying the powder.

* * * * *